United States Patent [19]

Liu

[11] Patent Number: 5,218,035

[45] Date of Patent: Jun. 8, 1993

[54] PHOSPHATE-CONTAINING SURGICAL CEMENTS

[76] Inventor: Sung-Tsuen Liu, 29 Landing, Laguna Niguel, Calif. 92677

[21] Appl. No.: 829,891

[22] Filed: Feb. 3, 1992

[51] Int. Cl.$^5$ .................. C08K 3/32; C04B 35/00
[52] U.S. Cl. .................................. 524/414; 524/5; 523/116; 106/35; 106/690; 501/1; 501/45
[58] Field of Search ............ 524/5, 414; 106/35, 106/690; 501/1, 45; 523/116

[56] References Cited

U.S. PATENT DOCUMENTS

| | | | |
|---|---|---|---|
| 4,376,168 | 3/1983 | Takani et al. | 501/1 |
| 4,612,053 | 9/1986 | Brown et al. | 106/35 |
| 4,619,655 | 10/1986 | Hanker et al. | 623/1 |
| 4,668,295 | 5/1987 | Bajpai | 106/690 |
| 5,039,546 | 8/1991 | Chung et al. | 427/2 |

OTHER PUBLICATIONS

Ohwaki et al, "Experimental Studies on Hydroxyapatite As A Bioactive Cement For Its Application To The Cementless Prostheses", The Third WorldBiomaterials Congress, Apr. 21-25, 1988, p. 336.
Oonishi et al, "Fully Bioactive Bone Cement Using Tetra-Calcium-Phosphate and Collagen, The 17th Annual Meeting of the Society for Biomaterials," May 1-5, 1991, p. 306.
Sugihara et al, "Surface Bioactive Bone Cement Using Alpha-Tricalcium Phosphate and Collagen", The 17th Annual Meeting of the Society for Biomaterials, May 1-5, 1991, p. 188.

*Primary Examiner*—Paul R. Michl
*Assistant Examiner*—LaVonda R. DeWitt
*Attorney, Agent, or Firm*—Frank J. Uxa

[57] ABSTRACT

New surgical cements for use in medical applications such as orthopedic and maxillofacial surgeries and dental applications are disclosed. These surgical cements comprise a hardened cement formed from a mixture comprising a cementing component selected from the group consisting of ceramics having the formula $$w(RO){-}x(R_2O){-}y(P_2O_5){-}z(X)$$

wherein RO is selected from the group consisting of CaO and mixtures of CaO and MgO, $R_2O$ is selected from the group consisting of alkali metal oxides and mixtures thereof, X is selected from the group consisting of $SO_4$ and Cl, and w, x, y and z are the mole fractions of the respective constituents in the ceramic, when X is $SO_4$, w is in the range of about 0.25 to about 0.5, x is in the range of about 0.05 to about 0.4, y is in the range of about 0.05 to about 0.25 and z is in the range of about 0.01 to about 0.25, and when X is Cl, w is in the range of about 0.25 to about 0.5, x is in the range of about 0.05 to about 0.5, y is in the range of about 0.1 to about 0.25 and z is in the range of about 0.01 to about 0.4 and mixtures thereof; a setting component selected from the group consisting of polyfunctional carboxylic acids containing 2 to about 10 carbon atoms, salts thereof, monobasic phosphate salts and mixtures thereof; and water in an amount effective to form a paste from the mixture which paste hardens into the hardened cement which is biocompatible.

20 Claims, No Drawings

PHOSPHATE-CONTAINING SURGICAL CEMENTS

BACKGROUND OF THE INVENTION

This invention relates to new calcium-phosphate-containing mixed ceramics and to surgical cements derived from such ceramics and certain setting components. The cements of this invention have reasonable, and preferably controllable, setting times and are easy to manipulate. By mixing the cementing component and setting component with water, a viscous and cohesive or adhesive paste is formed which becomes hard and sets, preferably in less than about 30 minutes. These cements can be readily used as or in a binder system or as a drug delivery system in granule forms of hard tissue implant materials. The present cements are useful in orthopedic and maxillofacial surgeries and in dental applications.

Bioglass and calcium phosphate ceramics have been confirmed as excellent biocompatible hard tissue implant materials. Among these calcium phosphate ceramics, hydroxyapatite and certain tricalcium phosphate ceramics have been commercialized. Most of these hard tissue implant materials are prepared in either block form or granule form. Similar to ceramic materials in general, such block forms of bioceramic are very brittle and very difficult to shape. On the other hand, the granule form of such materials has mobility problems. In the past many attempts have been made to solve these problems and to expand the medical applications of bioceramic materials by developing binder or cementing materials. Among the materials which have been suggested are collagen, polylactate, Plaster of Paris, polyacrylate, and calcium phosphate grout, paste and cementing materials.

Ideally, the binder or cement system should have the following characteristics: good biocompatibility, be moldable at the surgical site, be easy to manipulate, have a reasonable and controllable setting rate, and be bioresorbable. Most of the binder systems or cementing materials have certain disadvantages. For example, collagen and polylactate can be used as binders in granule forms of hydroxyapatite ceramics or other bioceramics, but such materials can be prepared only as premolded shapes. Plaster of Paris can be moldable at the surgical site, but it is usually resorbed too fast to match the bone growth. Polyacrylate and hydroxyapatite cements are non-resorbable.

The surgeon is most interested in surgical implant cements that can be shaped and hardened in situ. However, such preparations are not yet available. Recently, a number of attempts have been made using calcium phosphate ceramics to prepare grout, paste and cementing materials. Calcium phosphate pastes or grouts which can not harden in situ are useless for hard tissue implant because they disintegrate very quickly, for example, in the presence of water. Several calcium phosphate cements which harden have been proposed. All these cements are prepared by the reaction of single calcium phosphate ceramics with acidic setting reagents. In most cases, these cements are very acidic, which detracts from their biocompatibility. In addition, it is very difficult, if not impossible, to control the setting rate, mechanical strength and bioresorption of these cements.

It would clearly be advantageous to provide new surgical cements.

SUMMARY OF THE INVENTION

New surgical cements have been discovered. The present surgical cements are formed from mixtures comprising new calcium-phosphate-containing mixed ceramics as cementing components, certain setting components and water. By mixing the cementing components, setting components and water, a paste, preferably a highly viscous and cohesive or adhesive paste, is formed which can be set or hardened in situ, preferably with a controllable setting time, more preferably in the range of about 30 minutes or less. These cements have an initial surface pH of about 5 or higher and reach neutral (a surface pH of about 7) in a short period of time, for example, in the range of about 48 hours or less, in an aqueous environment. The cements of this invention can be compounded to provide great flexibility. For example, the compositions and/or concentrations of the cementing components and the setting components, as well as one or more other components in the paste-forming mixture, can be varied to control the setting rate and resorption rate.

In one embodiment, the cementing component is selected from the group consisting of one or more (one or a mixture of) ceramics having the formula

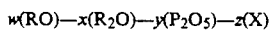

$$w(RO)-x(R_2O)-y(P_2O_5)-z(X)$$

wherein RO is selected from CaO and mixtures of CaO and MgO, $R_2O$ is selected from alkali metal oxides and Cl (chloride) and w, x, y and z are the mole fractions of the respective constituents in the ceramic. When X is $SO_4$, w is about 0.25 to about 0.5, x is about 0.05 to about 0.4, preferably about 0.12 to about 0.38, y is about 0.05 to about 0.25, preferably about 0.12 to about 0.25, and z is about 0.01 to about 0.25. When X is Cl, w is about 0.25 to about 0.5, x is about 0.05 to about 0.5, y is about 0.1 to about 0.25 and z is about 0.01 to about 0.4. In this embodiment, the setting component is selected from polyfunctional carboxylic acids containing 2 to about 10 carbon atoms, acidic salts thereof, monobasic phosphate salts and mixtures thereof. Such setting components are preferably water soluble. The water in the paste-forming mixture is present in an amount effective to form a paste from the mixture which paste sets or hardens into a hardened cement. The hardened cement is biocompatible.

In another embodiment, the cementing component is selected from the group consisting of one or more (one or a mixture of) ceramics having the formula

$$w(RO)-x(R_2O)-y(P_2O_5)$$

wherein RO is selected from CaO and mixtures of CaO and MgO, $R_2O$ is selected from alkali metal oxides and mixtures thereof, and w, x, y are the mole fractions of the respective constituents in the ceramic. In this formula, w is about 0.3 to about 0.85, x is about 0.05 to about 0.6 and y is about 0.05 to about 0.3. The setting component is selected from tartaric acid, tartrates, monobasic phosphate salts and mixtures thereof. Such setting components are preferably water soluble. The water in the paste-forming mixture is present in an amount effective to form a paste from the mixture which paste sets or hardens into a hardened cement. The hardened cement is biocompatible.

The preferred setting components for use with the sulfate and/or chloride containing ceramics are selected from citric acid, citrates, tartaric acid, tartrates, monobasic phosphates, such as monobasic calcium phosphate ($Ca(H_2PO_4)_2$), hydrates thereof and mixtures thereof. The preferred setting components for use with the other ceramics defined herein (,e.g., those which are substantially free of sulfate and chloride) are selected from tartaric acid, tartrates, monobasic phosphate salts, such as monobasic calcium phosphate ($Ca(H_2PO_4)_2$), hydrates thereof and mixtures thereof, more preferably tartaric acid. These setting components alone can interact, for example, chemically react, with the cementing components described herein in the presence of water to form a paste which can set in a rather short time period. The mixture preferably includes setting time modifier components, preferably water soluble setting time modifier components, other than the setting component used which may, and preferably do, also interact with the cementing components, that is which are involved in cement formation. The major function of such setting time modifier components is to control the setting rate of the paste. The preferred setting time modifier components include citric acid, malic acid, citrates, malates and mixtures thereof.

It is important that the final surgical cements, and preferably each of the components of the precursor mixture (in particular, if the cement is to be set or hardened in situ), be biocompatible.

The present invention permits manipulation of the moldable cementing pastes at the surgical site for hard tissue replacement with reasonable, and preferably controllable, setting times. The present cements can also be prepared as premolded shapes. For medical applications, the present cements can be used alone as bioresorbable implant materials or used as binder systems in granule forms of bioceramics or bioglass. These cements can serve as hard tissue replacement materials in orthopedic and maxillofacial surgeries and in dental applications.

DETAILED DESCRIPTION OF THE INVENTION

There are many types of pure calcium phosphate ceramics. Among these are dibasic calcium phosphate, calcium pyrophosphate, alpha-tricalcium phosphate, beta-tricalcium phosphate, hydroxyapatite and tetracalcium phosphate. Each of these pure calcium phosphate ceramics has its own unique physical and chemical properties. The solubility as well as the dissolution rate of each of these pure ceramics is quite different, one from the other. Most of the calcium phosphate cements are prepared by the interaction of pure calcium phosphate ceramics having a Ca/P ratio of greater than 1 with acidic setting reagents. Whether or not a calcium phosphate cement can be hardened in a reasonable (workable) time depends very strongly on the specific pure calcium phosphate ceramic used and the setting reagent selected. For example, alpha-tricalcium phosphate can interact with citric acid to form cement in several minutes, while the hydroxyapatite and citric acid mixture paste will not set at all. The differences in the solubility, dissolution rate and reaction rate of the calcium phosphates are at least partially responsible for the differences of their setting behavior. In a pure calcium phosphate cement system, it is rather difficult to control the setting rate and setting behavior of the paste and the resorption rate of the cement product.

In the present invention, calcium-phosphate-containing ceramics are used as cementing components. These ceramics include RO (calcium oxide or a mixture of calcium oxide and magnesium oxide) —$R_2O$ (alkali oxide)- $P_2O_5$-containing ceramics and RO (calcium oxide or a mixture of calcium oxide and magnesium oxide)- $R_2O$ (alkali oxide)- $P_2O_5$—X-containing ceramics. These ceramics can be prepared by a process which comprises contacting two or more components (that is components which provide the requisite amounts of the elements to make up or form the desired final ceramic) at conditions, including elevated temperature, for example, in the range of about 1200° C. to about 1450° C., preferably calcining or sintering conditions, effective to form the desired ceramic from the solid state reaction of the two or more components. Such method is illustrated as follows. The $CaO$—$Na_2O$—$P_2O_5$-containing ceramics are prepared by mixing the required amounts of $CaCO_3$, $Na_2CO_3$ and $(NH_4)_2HPO_4$ to provide a $CaO$:$Na_2O$:$P_2O_5$ mole ratio of 0.5:1:0.5. The mixture is then mixed and stirred with water to form a homogenous paste. This paste is dried, for example, on a hot plate, and the dried material is ground to a fine powder. This homogeneous mixed powder is then calcined at 1385° C. for one hour. After that, the final sintered mixed ceramic is cooled slowly to room temperature. This ceramic having a formula: 0.25 $CaO$-0.5 $Na_2O$-0.25 $P_2O_5$ is identified as Ceramic 1. By a similar procedure, a ceramic having the following formula:

$$0.312\ CaO\text{-}0.344\ Na_2O\text{-}0.156\ P_2O_5\text{-}0.188SO_4$$

was prepared by mixing required amounts of $(NH_4)_2HPO_4$, $Na_2CO_3$, $CaCO_3$ and $Na_2SO_4$. This second ceramic was identified as Ceramic 2. A ceramic similar to Ceramic 2 except containing chloride rather than sulfate can be prepared by replacing the $Na_2SO_4$ with a desired amount of NaCl.

The present invention provides great flexibility in that substantial variations in the composition of the ceramic are possible. This, in turn, provides advantages over single pure calcium phosphate ceramic systems. For RO-($R_2O$)-$P_2O_5$ ceramics, compositions, in terms of mole fractions, preferably range from about 0.25 to about 0.85 RO, about 0.05 to about 0.5 $R_2O$ and about 0.05 to about 0.25 $P_2O_5$.RO is calcium oxide or a mixture of calcium oxide and magnesium oxide, for example up to about 40% by weight of magnesium oxide. Preferably RO is CaO. The presently useful ceramics have a wide range of solubilities and dissolution rates toward cement formation. Furthermore, the different ceramic compositions can be used to advantage in controlling the resorption rate of the final cement.

The setting components useful with the sulfate and-/or chloride-containing ceramics in the present invention are selected from the group consisting of polycarboxylic acids containing 2 to about 10 carbon atoms, salts thereof, monobasic phosphate salts and mixtures thereof The polyfunctional carboxylic acids used in the present invention may be saturated or unsaturated. Representative examples of these acids include citric acid, alpha-ketoglutaric acid, pyruvic acid, oxalic acid, tartaric acid, succinic acid, fumaric acid, malic acid, oxalacetic acid, etc. Such polyfunctional acids include acids having a pK (first proton) of less than about 5.0. Preferred setting components for use with the sulfate/chloride containing ceramics include citric acid, citrates, tartaric acid, tartrates, monobasic phosphate salts and mixtures thereof. Tartaric acid is one particularly useful setting component.

The setting components useful with the other ceramics, e.g., the sulfate/chloride-free ceramics, defined herein are selected from tartaric acid, tartrates, monobasic phosphate salts and mixtures thereof. These setting agents are preferably water soluble.

With regard to the presently useful monobasic phosphate salts, such salts may be anhydrous and/or one or more hydrated forms of such salts. Monobasic calcium phosphate, hydrates thereof and mixtures thereof are particularly useful monobasic phosphate setting components.

The cation or cations associated with the setting component salt or salts should be such as to be biocompatible, and preferably should not substantially inhibit or restrict the water solubility of the salt or salts. Examples of useful cations include ammonium ions, alkali metal ions, such as sodium ions, potassium ions and the like ions, alkaline earth metal ions, such as calcium ions, magnesium ions and the like ions, and mixtures thereof.

The presently useful setting components, for example, such as tartaric acid, monobasic calcium phosphate and mixtures thereof, can be used alone but are advantageously used in combination with setting time modifier components which are other than, that is distinct from, the setting component being employed, and which are present in the paste-forming mixture in an amount effective to modify the rate at which the mixture is hardened relative to a substantially identical mixture without the setting rate modifier component. Particularly useful setting rate modifier components include citric acid, malic acid, citrates, malates and mixtures thereof.

The cation or cations associated with the setting time modifier component salt or salts should be such as to be biocompatible, and preferably should not substantially inhibit or restrict the water solubility of such salt or salts. Examples of useful cations include ammonium ions, alkali metal ions, such as sodium, potassium and the like ions, alkaline earth metal ions, such as calcium ions, magnesium ions and the like, ferrous ions, ferric ions and the like ions.

The amount of setting component, or the amount of the combination of setting component and setting time modifier component, should be such as to provide a paste which hardens in a desired setting time and provide a cement with acceptable properties. Preferably the weight ratio of the cementing component to the setting component, and preferably to the combination of the setting component plus the setting time modifier component, is in the range of about 5:1 to about 1.5:1.

For further controlling the bioresorption rate, a biocompatible filler component may be included in the paste-forming mixture. The filler component used can be in the form of particles, for example, granules or powder. Such particles can range, for example from about 3 microns to about 150 microns or about 200 microns or about 400 microns in size. Both bioresorbable and non-resorbable filler components can be used. The weight ratio of filler component to cementing component can be up to about 4:1. Exemplary filler components included calcium-containing apatites, hydroxyapatite, bioglass, calcium fluoride, tricalcium phosphate, dibasic calcium phosphate, calcium sulfate, collagen and mixtures thereof.

For formulation, the cementing component and one or more or all of the solid components of the present paste-forming mixtures can be mixed to form a solid mixture, e.g., a mixed powder. To prepare the cement, the solid mixture is pasted with the required amount of water, for example, in the form of a saline solution, to form a viscous and adhesive paste which can be hardened and set. Alternatively, the cementing component and insoluble setting component, such as monobasic calcium phosphate, can be premixed. The soluble setting component and/or setting time modifier component can be predissolved in water to form a setting solution. The premixed solid mixture is stirred and mixed with certain amounts of the setting solution to form a curable paste.

For application, the present cements can be prepared as a moldable paste and introduced into the surgical site before being hardened. Alternatively, it can be prepared as a premolded shape for implantation. For application as a drug delivery system, the drug can be incorporated into the cementing paste. After the paste is set, the hardened cement can be broken into granule form. This drug-containing granules are dried and stored for use.

The cement of the present invention can be used in orthopedic and maxillofacial surgeries and dental applications. These include, for example, 1) as hard tissue replacement materials such as bone graft, bone defect filler or bone substitute material, 2) ridge augmentation, 3) bone fracture fraction, 4) luting cement for dentistry and orthopedic surgery, 5) bone cement and root cement 6) bone wax substitute material, 7) jaw repair, 8) drug delivery system. Antibiotic (up to about 20% by weight of the cement) and bone growth proteins (up to about 10% by weight of the cement) are preferred drugs to be released by the cement of this invention.

The invention is illustrated in more detail in the following non-limiting examples.

EXAMPLES 1 TO 8

Ceramic 1, prepared as described above, was ground and passed through 100 mesh. 0.1 g of tartaric acid was dissolved in 0.15 ml deionized water to form a setting solution. 0.5 g of Ceramic 1 was then stirred and mixed with the setting solution. The paste became viscous and adhesive and set after about 5 minutes. The surface pH of the setting cement was initially at about 5 and reached near neutral in a very short time period.

A series of seven (7) additional cements were similarly prepared from Ceramic 1 using various setting components and setting time modifier components. Results of these cements, together with the results of the cement from Example 1, are listed in Table 1.

TABLE 1

| Example No. | Ceramic 1 used (g) | Setting Component (g) | Setting Time Modifier Component (g) | $H_2O$ (ml) | Setting Time (min) |
|---|---|---|---|---|---|
| 1 | 0.5 | 0.1 g tartaric acid | 0 | 0.15 | 5 |
| 2 | 0.5 | 0.2 g tartaric acid | 0.03 g malic acid | 0.15 | 25 |
| 3 | 0.5 | 0 | 0.1 g malic acid | 0.12 | >30 |
| 4 | 0.5 | 0.1 g $Ca(H_2PO_4)_2$ | 0 | 0.15 | <1 |
| 5 | 0.5 | 0.1 g $Ca(H_2PO_4)_2$ | 0.1 g malic acid | 0.14 | >15 |
| 6 | 0.5 | 0.3 g | 0.1 g | 0.15 | 3 |

TABLE 1-continued

| Example No. | Ceramic 1 used (g) | Setting Component (g) | Setting Time Modifier Component (g) | H$_2$O (ml) | Setting Time (min) |
| --- | --- | --- | --- | --- | --- |
| | | Ca(H$_2$PO$_4$)$_2$ | malic acid | | |
| 7 | 0.5 | 0.2 g Ca(H$_2$PO$_4$)$_2$ | 0.05 g citric acid | 0.15 | 5 |
| 8 | 0.5 | 0 | 0.1 citric acid | 0.15 | >30 |

EXAMPLES 9 TO 15

Ceramic 2, prepared as described above, was ground and passed through 100 mesh. 0.5 g of Ceramic 2 was mixed with 0.25 g tartaric acid powder. The mixed powder was then stirred and mixed with 0.18 ml of deionized water and formed a stickey paste which became set at about 1.5 minutes.

A series of six (6) additional cements were similarly prepared from Ceramic 2 using various setting components and setting time modifier components. Results of these cements (and the result from the cement of Example 9) are listed in Table 2.

TABLE 2

| Example No. | Ceramic 2 used (g) | Setting Component (g) | Setting Time Modifier Component (g) | H$_2$O (ml) | Setting Time (min) |
| --- | --- | --- | --- | --- | --- |
| 9 | 0.5 | 0.25 g tartaric acid | 0 | 0.18 | 1.5 |
| 10 | 0.5 | 0.1 g tartaric acid | 0.1 g malic acid | 0.13 | >180 |
| 11 | 0.5 | 0.2 g Ca(H$_2$PO$_4$)$_2$ | 0 | 0.15 | 1 |
| 12 | 0.5 | 0.2 Ca(H$_2$PO$_4$)$_2$ | 0.05 g malic acid | 0.13 | 1 |
| 13 | 0.5 | 0.2 g Ca(H$_2$PO$_4$)$_2$ | 0.1 g malic acid | 0.15 | 3 |
| 14 | 0.5 | 0.2 g Ca(H$_2$PO$_4$)$_2$ | 0.15 g malic acid | 0.15 | 8 |
| 15 | 0.5 | 0.2 g Ca(H$_2$PO$_4$)$_2$ | 0.03 g citric acid | 0.13 | 5 |

These result demonstrate that by varying the composition of the surgical cements of the present invention the setting rate can be easily controlled. The present cements are biocompatible, easy to manipulate, have advantageous surface pH characteristics, can be set in situ or premolded into shapes, and can be used in granule form, for example, as a binder system and/or as a drug delivery system.

While this invention has been described with respect to various specific examples and embodiments, it is to be understood that the invention is not limited thereto and that it can be variously practiced within the scope of the following claims.

What is claimed is:

1. A surgical cement for use in medical applications such as orthopedic and maxillofacial surgeries and dental applications comprising a hardened cement formed from a mixture comprising a cementing component selected from the group consisting of ceramics having the formula $$w(RO)-x(R_2O)-y(P_2O_5)-z(X)$$

wherein RO is selected from the group consisting of CaO and mixtures of CaO and MgO, R$_2$O is selected from the group consisting of alkali metal oxides and mixtures thereof, X is selected from the group consisting of SO$_4$ and Cl, and w, x, y and z are the mole fractions of the respective constituents in said ceramic, when X is SO$_4$, w is in the range of about 0.25 to about 0.5, x is in the range of about 0.05 to about 0.4, y is in the range of about 0.05 to about 0.25 and z is in the range of about 0.01 to about 0.25, and when X is Cl, w is in the range of about 0.25 to about 0.5, x is in the range of about 0.05 to about 0.5, y is in the range of about 0.1 to about 0.25 and z is in the range of about 0.01 to about 0.4, and mixtures thereof; a setting component selected from the group consisting of polyfunctional carboxylic acids containing 2 to about 10 carbon atoms, acidic salts thereof, monobasic phosphate salts and mixtures thereof; and water in an amount effective to form a paste from said mixture which paste hardens into said hardened cement which is biocompatible.

2. The surgical cement of claim 1 wherein the weight ratio of said cementing component to said setting component in said mixture is in the range of about 5:1 to about 1.5 to 1, and said mixture hardens in about 30 minutes or less after said paste is formed.

3. The surgical cement of claim 1 wherein R$_2$O is selected from the group consisting of Na$_2$O, K$_2$O and mixtures thereof.

4. The surgical cement of claim 1 wherein X is SO$_4$, x is in the range of about 0.12 to about 0.38, and y is in the range of about 0.12 to about 0.25.

5. The surgical cement of claim 1 wherein said setting component is selected from the group consisting of citric acid, citrates, tartaric acid, tartrates monobasic phosphate salts and mixtures thereof.

6. The surgical cement of claim 1 wherein said setting component is selected from the group consisting of Ca(H$_2$PO$_4$)$_2$, hydrates thereof and mixtures thereof.

7. The surgical cement of claim 1 wherein said setting component is tartaric acid.

8. The surgical cement of claim 1 wherein said mixture further comprises a setting rate modifier component in an amount effective to modify the rate at which said mixture is hardened relative to a substantially identical mixture without said setting rate modifier component.

9. The surgical cement of claim 8 wherein said setting rate modifier component is other than said setting component and is selected from the group consisting of citric acid, malic acid, citrates, malates and mixtures thereof 10. The surgical cement of claim 1 wherein said mixture further comprises a biocompatible filler component wherein the amount of filler component is such that the weight ratio of said filler component to said cementing component is about 4:1 or less.

11. A surgical cement for use in medical applications such as orthopedic and maxillofacial surgeries and dental applications comprising a hardened cement formed from a mixture comprising a cementing component selected from the group consisting of ceramics having the formula $$w(RO)-x(R_2O)-y(P_2O_5)$$

wherein RO is selected from the group consisting of CaO and mixtures of CaO and MgO, $R_2O$ is selected from the group consisting of alkali metal oxides and mixtures thereof, and w, x, y and z are the mole fractions of the respective constituents in said ceramic wherein w is in the range of about 0.2 to about 0.85, x is in the range of about 0.05 to about 0.6, and y is in the range of about 0.05 to about 0.3, and mixtures thereof; a setting component selected from the group consisting of tartaric acid, tartrates, monobasic phosphate salts and mixtures thereof; and water in an amount effective to form a paste from said mixture which paste hardens into said hardened cement which is biocompatible.

12. The surgical cement of claim 11 wherein the weight ratio of said cementing component to said setting component in said mixture is in the range of about 5:1 to about 1.5 to 1, and said mixture hardens in about 30 minutes or less after said paste is formed.

13. The surgical cement of claim 11 wherein $R_2O$ is selected from the group consisting of $Na_2O$, $K_2O$ and mixtures thereof.

14. The surgical cement of claim 11 wherein RO is CaO.

15. The surgical cement of claim 1 wherein said setting component is selected from the group consisting of tartaric acid, $Ca(H_2PO_4)_2$, hydrates thereof and mixtures thereof.

16. The surgical cement of claim 11 wherein said mixture further comprises a setting rate modifier component in an amount effective to modify the rate at which said mixture is hardened relative to a substantially identical mixture without said setting rate modifier component.

17. The surgical cement of claim 16 wherein said setting rate modifier component is selected from the group consisting of citric acid, malic acid, citrates, malates and mixtures thereof.

18. The surgical cement of claim 11 wherein said mixture further comprises a biocompatible filler component wherein the amount of filler component is such that the weight ratio of said filler component to said cementing component is about 4:1 or less.

19. A composition for use in medical applications such as orthopedic and maxillofacial surgeries and dental applications comprising ceramic having the following formula $$w(RO)-x(R_2O)-y(P_2O_5)-z(X)$$

wherein RO is selected from the group consisting of CaO and mixtures of CaO and MgO, $R_2O$ is selected from the group consisting of alkali metal oxides and mixtures thereof, X is selected from the group consisting of $SO_4$ and Cl, and w, x, y and z are the mole fractions of the respective constituents in said ceramic, when X is $SO_4$, w is in the range of about 0.25 to about 0.5, x is in the range of about 0.05 to about 0.4, y is in the range of about 0.05 to about 0.25 and z is in the range of about 0.01 to about 0.25; and when X is Cl, w is in the range of about 0.25 to about 0.5, x is in the range of about 0.05 to about 0.5, y is in the range of about 0.1 to about 0.25 and z is in the range of about 0.01 to about 0.4, and mixtures thereof.

20. The composition of claim 19 wherein X is $SO_4$, x in the range of about 0.12 to about 0.38, and y is in the range of about 0.12 to about 0.25.

* * * * *

UNITED STATES PATENT AND TRADEMARK OFFICE
CERTIFICATE OF CORRECTION

PATENT NO. : 5,218,035
DATED : June 8, 1993
INVENTOR(S) : Liu

It is certified that error appears in the above-identified patent and that said Letters Patent is hereby corrected as shown below:

Column 2, line 32, after "and" insert -- mixtures thereof, X is selected from $SO_4$ (sulfate) and --

Column 4, line 59; after "thereof" insert --.--

Column 7, line 21; delete "stickey" and insert in place thereof --sticky--

Signed and Sealed this

Eighteenth Day of January, 1994

Attest:

BRUCE LEHMAN

Attesting Officer

Commissioner of Patents and Trademarks